US012765926B2

(12) United States Patent
Louvis et al.

(10) Patent No.: US 12,765,926 B2

(45) Date of Patent: Oct. 20, 2026

(54) SYSTEM AND METHODS FOR HIP FRACTURE FIXATION WITH BOLT SYNCHRONIZATION

(71) Applicant: Stryker European Operations Limited, Carrigtwohill (IE)

(72) Inventors: Eleftherios Louvis, Carrigaline (IE); Antonio Zanotti, Midleton (IE); Bernd Simon, Kiel (DE)

(73) Assignee: Stryker European Operations Limited, Carrigtwohill (IE)

( * ) Notice: Subject to any disclaimer, the term of this patent is extended or adjusted under 35 U.S.C. 154(b) by 0 days.

(21) Appl. No.: 19/042,822

(22) Filed: Jan. 31, 2025

(65) Prior Publication Data

US 2026/0090830 A1 Apr. 2, 2026

(30) Foreign Application Priority Data

Oct. 2, 2024 (GR) .............................. 20240100685

(51) Int. Cl.
*A61B 17/74* (2006.01)
*A61B 17/72* (2006.01)

(52) U.S. Cl.
CPC ........ *A61B 17/744* (2013.01); *A61B 17/7225* (2013.01); *A61B 17/725* (2013.01)

(58) Field of Classification Search
CPC . A61B 17/7426; A61B 17/742; A61B 17/744; A61B 17/746
See application file for complete search history.

(56) References Cited

U.S. PATENT DOCUMENTS

| | | | |
|---|---|---|---|
| 3,374,786 | A | 3/1968 | Callender, Jr. |
| 5,429,641 | A | 7/1995 | Gotfried |
| 5,514,138 | A | 5/1996 | Mccarthy |
| 6,221,074 | B1 | 4/2001 | Cole et al. |
| 6,423,066 | B1 | 7/2002 | Harder et al. |
| 6,648,889 | B2 | 11/2003 | Bramlet et al. |
| 6,921,400 | B2 | 7/2005 | Sohngen |

(Continued)

FOREIGN PATENT DOCUMENTS

| | | | |
|---|---|---|---|
| WO | 2006092593 | A1 | 9/2006 |
| WO | 2023147608 | A1 | 8/2023 |

(Continued)

OTHER PUBLICATIONS

International Search Report issued in Appln. No. PCT/IB2025/000506 dated Jan. 30, 2026 (8 pages).

*Primary Examiner* — Eduardo C Robert
*Assistant Examiner* — Anna V. Little
(74) *Attorney, Agent, or Firm* — Lerner David LLP

(57) ABSTRACT

A fracture fixation system includes an implant defining a transverse bore extending along a bore axis, the bore being defined by first and second passages that each extend along the bore axis. The fracture fixation system further includes a lag screw configured to be inserted through the second passage, wherein a distal portion of the lag screw includes a thread. The fracture fixation system further includes a bolt configured to be inserted through the first passage, wherein a lateral side of the bolt defines a negative thread adapted to receive the thread of the lag screw. The negative thread includes a transition portion configured to align the thread of the lag screw with the negative thread of the bolt.

16 Claims, 14 Drawing Sheets

(56) References Cited

U.S. PATENT DOCUMENTS

| | | | |
|---|---|---|---|
| 6,926,719 B2 | 8/2005 | Sohngen et al. | |
| 7,135,023 B2 | 11/2006 | Watkins et al. | |
| 7,247,157 B2 | 7/2007 | Prager et al. | |
| 7,410,488 B2 | 8/2008 | Janna et al. | |
| 7,527,627 B2 | 5/2009 | Ferrante et al. | |
| 7,534,244 B2 | 5/2009 | Ferrante et al. | |
| 7,655,009 B2 | 2/2010 | Grusin | |
| 7,780,667 B2 | 8/2010 | Watanabe et al. | |
| 7,799,030 B2 | 9/2010 | Watanabe et al. | |
| 7,883,509 B2 | 2/2011 | Ferrante et al. | |
| 7,918,853 B2 | 4/2011 | Watanabe et al. | |
| 7,931,652 B2 | 4/2011 | Ferrante et al. | |
| 7,972,336 B2 | 7/2011 | James et al. | |
| 8,092,454 B2 | 1/2012 | Sohngen | |
| 8,105,326 B2 | 1/2012 | Ferrante et al. | |
| 8,114,078 B2 | 2/2012 | Aschmann | |
| 8,114,079 B2 | 2/2012 | Haidukewych et al. | |
| 8,177,786 B2 | 5/2012 | Leyden et al. | |
| 8,182,484 B2 | 5/2012 | Grant et al. | |
| 8,187,275 B2 | 5/2012 | Ferrante et al. | |
| 8,241,286 B2 | 8/2012 | Metzinger et al. | |
| 8,257,361 B2 | 9/2012 | Ritchey et al. | |
| 8,298,234 B2 | 10/2012 | Ferrante et al. | |
| 8,308,732 B2 | 11/2012 | Millett et al. | |
| 8,394,103 B2 | 3/2013 | O'Reilly et al. | |
| 8,398,636 B2 | 3/2013 | Simon et al. | |
| 8,449,544 B2 | 5/2013 | Grusin | |
| RE44,501 E | 9/2013 | Janna et al. | |
| 8,551,093 B2 | 10/2013 | Roth et al. | |
| 8,617,161 B2 | 12/2013 | Ferrante et al. | |
| 8,628,531 B2 | 1/2014 | Ritchey et al. | |
| 8,628,532 B2 | 1/2014 | Ritchey et al. | |
| 8,702,707 B2 | 4/2014 | Sohngen | |
| 8,715,283 B2 | 5/2014 | Brumfield et al. | |
| 8,734,494 B2 | 5/2014 | Simon et al. | |
| 8,764,752 B2 | 7/2014 | Buettler et al. | |
| 8,771,271 B2 | 7/2014 | Overes | |
| 8,834,469 B2 | 9/2014 | Watanabe et al. | |
| 8,840,675 B2 | 9/2014 | Song | |
| 8,845,648 B2 | 9/2014 | Guzman et al. | |
| 8,932,301 B2 | 1/2015 | Metzinger et al. | |
| 8,939,978 B2 | 1/2015 | Watanabe et al. | |
| 8,945,136 B2 | 2/2015 | Overes | |
| 9,084,643 B2 | 7/2015 | Mikhail et al. | |
| 9,155,582 B2 | 10/2015 | Felder et al. | |
| 9,220,544 B2 | 12/2015 | Matityahu et al. | |
| 9,247,975 B2 | 2/2016 | Erhart et al. | |
| 9,301,767 B2 | 4/2016 | Ritchey et al. | |
| RE46,008 E | 5/2016 | Janna et al. | |
| 9,339,311 B1 | 5/2016 | Tsai et al. | |
| 9,358,052 B2 | 6/2016 | Hansson | |
| RE46,078 E | 7/2016 | Janna et al. | |
| 10,058,337 B2 | 8/2018 | Feibel et al. | |
| 10,123,828 B2 | 11/2018 | Matityahu et al. | |
| 10,172,654 B2 | 1/2019 | Watanabe et al. | |
| 10,251,691 B2 | 4/2019 | Hedgeland et al. | |
| 10,299,847 B2 | 5/2019 | Rossney et al. | |
| 10,413,306 B2 | 9/2019 | Russell et al. | |
| 10,517,613 B2 | 12/2019 | Bouduban et al. | |
| 10,758,281 B2 | 9/2020 | Hansson | |
| 11,737,796 B2 | 8/2023 | Inan | |
| 11,771,480 B2 | 10/2023 | Laird et al. | |
| 11,779,382 B2 | 10/2023 | Dacosta et al. | |
| 12,004,785 B2 | 6/2024 | Shinde et al. | |
| 12,121,271 B2 | 10/2024 | White et al. | |
| 12,453,585 B2 | 10/2025 | Rakes et al. | |
| 12,458,418 B2 | 11/2025 | Shinde et al. | |
| 12,484,916 B2 | 12/2025 | Nader et al. | |
| 12,484,944 B2 | 12/2025 | Stockdill et al. | |
| 2006/0069392 A1 | 3/2006 | Renzi Brivio et al. | |
| 2006/0084999 A1 | 4/2006 | Aschmann | |
| 2007/0270845 A1 | 11/2007 | Watanabe et al. | |
| 2007/0270847 A1 | 11/2007 | Shaw | |
| 2008/0051790 A1 | 2/2008 | Defossez | |
| 2008/0183171 A1 | 7/2008 | Elghazaly et al. | |
| 2008/0281326 A1* | 11/2008 | Watanabe | A61B 17/164 606/65 |
| 2009/0248025 A1 | 10/2009 | Haidukewych et al. | |
| 2009/0264885 A1 | 10/2009 | Grant et al. | |
| 2009/0326534 A1 | 12/2009 | Yamazaki et al. | |
| 2011/0264150 A1 | 10/2011 | Hansson et al. | |
| 2012/0271309 A1 | 10/2012 | Watanabe et al. | |
| 2013/0046307 A1 | 2/2013 | Yang | |
| 2014/0012259 A1 | 1/2014 | Matityahu et al. | |
| 2017/0202584 A1 | 7/2017 | Hientzsch et al. | |
| 2018/0078299 A1 | 3/2018 | Rossney et al. | |
| 2018/0177538 A1 | 6/2018 | Hansson | |
| 2018/0250042 A1 | 9/2018 | Sato et al. | |
| 2019/0336186 A1 | 11/2019 | Tanaka et al. | |
| 2021/0259842 A1* | 8/2021 | Feng | A61B 17/7001 |
| 2025/0082375 A1 | 3/2025 | Rakes et al. | |
| 2025/0114107 A1 | 4/2025 | Myers et al. | |

FOREIGN PATENT DOCUMENTS

| | | |
|---|---|---|
| WO | 2023147609 A1 | 8/2023 |
| WO | 2025078262 A1 | 4/2025 |

* cited by examiner

SYSTEM AND METHODS FOR HIP FRACTURE FIXATION WITH BOLT SYNCHRONIZATION

CROSS-REFERENCE TO RELATED APPLICATIONS

The present application claims the benefit of the priority date of Greek patent application number 20240100685 filed Oct. 2, 2024, the disclosure of which is hereby incorporated by reference in its entirety.

FIELD OF THE INVENTION

The present invention relates to orthopedic surgical devices used to join and promote healing of fractured bone, and more particularly, and not by limitation, devices used to fixate proximal femoral fractures.

BACKGROUND OF THE INVENTION

The surgical treatment of femoral neck fractures utilizing internal fixation remains challenging, especially for dislocated unstable fractures. There are a variety of devices used to treat fractures of the femur, humerus, tibia, and other long bones. For example, fractures of the femoral neck, head, and intertrochanteric region have been successfully treated with a variety of internal fixation means such as compression screw assemblies. Compression hip and bone screw devices for use in fixating a fractured bone during the healing process have been used for years. It is mainstream practice for surgeons to utilize cannulated compression screws (CCS) or sliding hip screws (SHS) as compression screws in internal fixation systems.

For many surgeons and customers, the utilization of CCS or SHS devices remain the treatment of choice. However, CCS accounts for up to nearly 30% of hip fracture failures and their disadvantages are well documented. In particular, CCS devices are not angularly stable, have insufficient rotation control, and suffer from uncontrolled shortening of the femoral neck and limited resistance against shear forces. Disadvantages of SHS are that an additional anti-rotation screw is required with limited space particularly in small anatomies, that they have large lateral footprints, and also that they create a potential collision with a retrograde nail in the case of ipsilateral neck-shaft fixation.

Additionally, problems may result from weakened or poor-quality bone that is adjacent to the fracture site. Often times the bone adjacent to the fracture is weak and is prone to damage when exposed to compression. For example, there could be uncontrolled shortening of the femoral head when the femoral head compresses towards or into the fracture site. In extreme cases, uncontrolled shortening may cause the femoral head to be compressed all the way into the trochanteric region of the femur.

Thus, it would be desirable to provide a fracture fixation system to improve on the prior art disadvantages.

BRIEF SUMMARY OF THE INVENTION

According to a first aspect of the disclosure, a fracture fixation system may include an implant, a lag screw and a bolt. The implant may define a transverse bore extending along a bore axis. The bore may be defined by first and second passages that each extend along the bore axis. The lag screw may be configured to be inserted through the second passage. A distal portion of the lag screw may include a thread. The bolt may be configured to be inserted through the first passage. A lateral side of the bolt may define a negative thread adapted to receive the thread of the lag screw. The negative thread may include a transition portion configured to align the thread of the lag screw with the negative thread of the bolt.

Further in the first aspect of the disclosure, the implant may include a plate and a barrel. The plate may have an outer surface and an inner surface for placement against an exterior surface of a bone, and the barrel may extend along the bore axis and having a peripheral wall. The first and second passages may extend through the barrel. The implant may be an intramedullary nail. The negative thread of the bolt may be formed by a plurality of recesses in the lateral side of the bolt. Each of the plurality of recesses may be disposed between a pair of ridges of the bolt. Each of the ridges may protrude radially outward from a central longitudinal axis of the bolt relative to the plurality of recesses, and each recess may span a length along a direction of the central longitudinal axis between the pair of surrounding ridges. At least some of the plurality of recesses may have equal lengths relative to each other. At least some of the plurality of recesses may have varying lengths relative to each other.

Further in the first aspect of the disclosure, a first group of the plurality of recesses may have varying lengths relative to each other and a second group of the plurality of recesses may have equal lengths relative to each other. The second group may be positioned distal to the first group along the direction of the central longitudinal axis of the bolt. Each recess may define a width in a direction transverse to the length, and a magnitude of the length of each recess of the first group of the plurality of recesses may vary along the width of the respective recess. The plurality of recesses may include a first recess having a first length tapering along a width direction transverse to the length and a second recess located distal to the first recess may have a second length tapering along the width direction, the second length being less than the first length when the first and second lengths are measured along a single longitudinal axis of the bolt. The plurality of recesses may include a third recess located distal to the second recess having a third length constant along the width direction, the third length being less than the second length when the second and third lengths are measured along the longitudinal axis of the bolt.

Further in the first aspect of the disclosure, each recess may define a width in a direction transverse to the length, wherein the plurality of recesses includes a first group of recesses may have lengths tapering along their respective widths, and the plurality of recesses may include a second group of recesses having lengths which are constant along their respective widths. The second group of recesses may be positioned distal to the first group of recesses along a length of the bolt. The plurality of recesses may include a first recess bound by a first sidewall defined by a first ridge and a second sidewall defined by a second ridge, and the first sidewall may extend along a first plane and the second sidewall may extend along a second plane nonparallel to the first plane. The first plane may extend orthogonal to the central longitudinal axis of the bolt and the second plane may form an acute angle with the central longitudinal axis of the bolt. The plurality of recesses may include a second recess bound by a third sidewall defined by the second ridge and a fourth sidewall defined by a third ridge, and the third sidewall may extend along a third plane and the fourth sidewall may extend along a fourth plane nonparallel to the third plane. The fourth plane may extend orthogonal to the central longitudinal axis of the bolt and the third plane may form an acute angle with the central longitudinal axis of the bolt. The fourth plane may extend parallel to the second plane and the third plane may extend parallel to the first plane. The plurality of recesses may include a second recess bound by a third sidewall and a fourth sidewall, and the third sidewall and the fourth sidewall may be parallel. The second recess may be positioned distal to the first recess along a length of the bolt.

Further in the first aspect of the disclosure, the plurality of recesses may be spaced apart such that each recess is configured to receive a portion of the thread of the lag screw. A cross-section of the bolt taken perpendicular to a central longitudinal axis of the bolt and intersecting the negative thread of the bolt may be non-circular. The first sidewall may be chamfered. Each ridge may include a radial outer wall having a ridge length, and the bolt may include a first ridge having a first ridge length and the bolt may include a second ridge having a second ridge length greater than the first ridge length along the direction of the central longitudinal axis of the bolt, and the second ridge may be positioned distal to the first section. The first ridge length may taper along a circumference of the bolt. The plurality of recesses may be sized and spaced such that engagement of the thread of the lag screw with the negative thread causes axial displacement of the lag screw relative to the bolt to align the thread of the lag screw with the plurality of recesses when the lag screw is being coupled to the bolt. A thickness of the thread of the lag screw may taper as the thread extends toward the distal end of the lag screw. The first ridge length may taper to define an edge at which sidewalls of the first ridge meet at the edge at an end of the ridge.

According to a second aspect of the disclosure, a method of using a fracture fixation system may include drilling into a bone a first superior bore having a first diameter to a first depth; drilling into the bone a first inferior bore having a second diameter to a second length; installing an implant to the bone; inserting a bolt into a transverse bore defined through the implant such that a distal end of the bolt extends into one of the first superior bore and the first inferior bore; and inserting a lag screw into the transverse bore defined through the implant such that a distal end of the lag screw extends into the other one of the first superior bore and the first inferior bore. Inserting the lag screw may include rotating the lag screw to advance the lag screw distally relative to the bolt such that at thread of the lag screw engages with a transition portion of a negative thread of the bolt to align the thread of the lag screw with the negative thread of the bolt.

Further in the second aspect of the disclosure, the method may include drilling into the bone a second superior bore within the first superior bore to a third depth, the second superior bore having a third diameter smaller than the first diameter; and drilling into the bone a second inferior bore within the first inferior bore to a fourth depth, the second inferior bore having a fourth diameter smaller than the second diameter. Installing the implant to the bone may include placing an inner surface of a plate of the fixation element against an exterior surface of the bone and inserting a peripheral wall of a barrel of the fixation element into the first superior bore and the first inferior bore. Installing the implant to the bone may include inserting an intramedullary nail in an intramedullary canal of the bone. Inserting the bolt may include inserting the bolt into the first superior bore and inserting the lag screw may include inserting the lag screw into the first inferior bore. The step of inserting the bolt occurs before the step of inserting the lag screw. The step of inserting the bolt may include positioning a distal portion of the bolt in a femoral head.

Further in the second aspect of the disclosure, the lag screw may be advanced along a trajectory and the negative thread of the bolt may be sized and shaped to axially displace the lag screw from the trajectory to align the thread of the lag screw with the negative thread of the bolt. The negative thread of the bolt may include a plurality of recesses spaced apart along a length of the bolt and advancing the lag screw may include engaging the thread of the lag screw with a proximal recess of the plurality of recesses. Advancing the lag screw may include contacting the thread of the lag screw with a surface bounding the first recess to impart an axial force on the lag screw as the lag screw is rotated. The surface bounding the first recess may be at a proximal end of the first recess and may impart a distal axial force on the lag screw. The surface bounding the first recess may be at a distal end of the first recess and may impart a proximal axial force on the lag screw. Drilling the first superior bore may include reaming the first superior bore and drilling the second superior bore may include reaming the second superior bore.

Further in the second aspect of the disclosure, after the thread of the lag screw has engaged the negative thread of the bolt, rotating the lag screw may cause synchronization of the thread of the lag screw with the negative thread of the bolt. The method may further include pulling the lag screw proximally to compress a femoral neck fracture. Pulling the lag screw may be performed after the negative thread of the bolt and the thread of the lag screw are engaged. The method may further include coupling a tool to the bolt to control relative rotation between the bolt and the lag screw during insertion of the lag screw. Inserting the lag screw may include coupling a tool to the lag screw to control relative rotation between the bolt and the lag screw during insertion of the lag screw.

DETAILED DESCRIPTION

Figure 1:
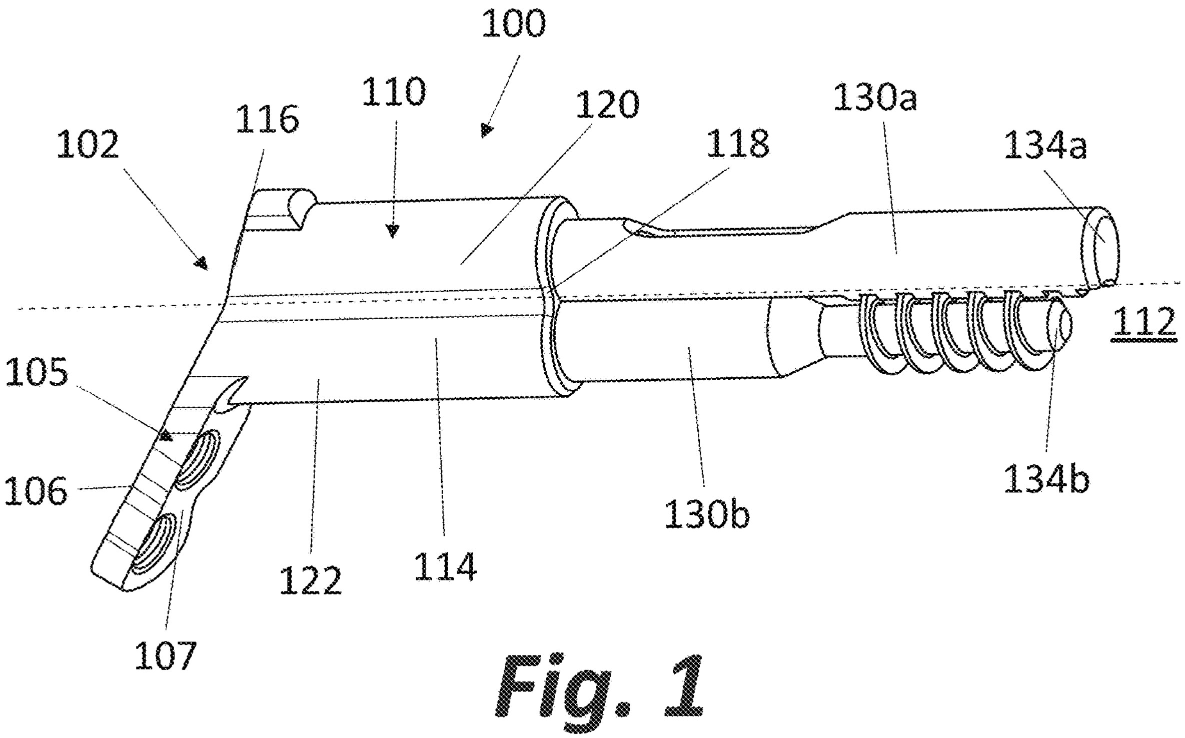
FIG. 1 is a side view of a fracture fixation system according to an embodiment of the disclosure.
Figure 2:
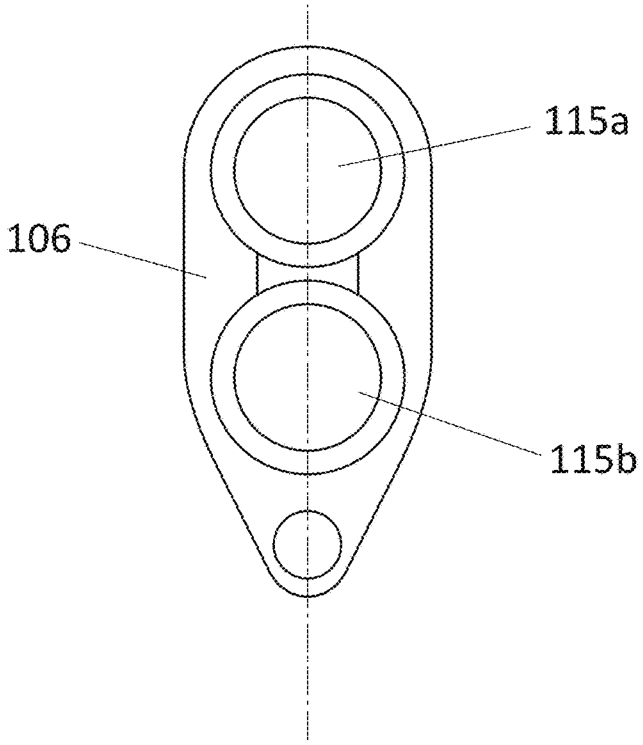
FIG. 2. is a rear view of a portion of the fracture fixation system of FIG. 1.

The present disclosure describes a fracture fixation system, preferably for a femoral fracture (e.g., femoral neck fractures) used particularly to mount and install on a femur to provide support for the femur and assist with healing of a proximal femoral fracture. The system and arrangement described herein may be incorporated in a fixation device positioned on a surface of bone and extending therethrough, i.e. a plate arrangement, or may alternatively be incorporated with an intramedullary nail extending longitudinally through the long bone. The fixation system will be primarily described with a fixation device mounted on a surface of the bone, but it should be appreciated that the concepts described with a fixation device can be similarly translated to use with an intramedullary nail.

The fixation device may include a barrel defining a passageway and adapted to receive a bolt and/or a lag screw. The bolts and lag screws are sized and shaped to fit within the passageway of the barrel and extend further distally through a distal opening in the barrel. The bolts and lag screws may be inserted into the passageway of the barrel without passing completely through the barrel, such that proximal ends of the bolts and lag screws are held or disposed within a portion of the barrel. It should be understood that the fracture fixation system described herein may be applied to long bones in general, and while directed to a femur in the present description, it may also be directed to a humerus, tibia and other long bones.

As used herein, the term "proximal," when used in connection with a device or components of a device, refers to the end of the device closer to the user of the device (e.g., surgeon or operator) when the device is being used as intended. On the other hand, the term "distal," when used in connection with a device or components of a device, refers to the end of the device farther away from the user (e.g., surgeon or operator) when the device is being used as intended. As used herein, the term "superior" refers to an upward direction on the page or relative to an anatomy of a person standing upright. On the other hand, the term "inferior" refers to a downward direction on the page or relative to an anatomy of a person standing upright. It should be understood that these terms are not limiting, but merely used for ease of description, and that varied orientations may cause directions to differ. As used herein, the terms "substantially, "generally," "approximately" and "about" are intended to mean that slight deviations from absolute are included within the scope of the term so modified.

FIGS. 1-16 illustrate a fracture fixation system 100 according to an embodiment of the disclosure. The fracture fixation system 100 includes a fixation element 102 having a plate 105 defining an outer surface 106 and an inner surface 107 adapted for placement against an exterior of the femur when the fixation system 100 is in use. The fixation element 102 further includes a barrel 110 extending from a barrel proximal end 116 to a barrel distal end 118 along a barrel axis 112 and having a peripheral wall 114 that forms an outer surface of the barrel 110. The barrel 110 may be manufactured based on patient-specific data to a particular size, shape and profile, which aids in effectively controlling varus forces.

The fixation system 100 is used with a proximal femur 50 (shown in FIGS. 9-11), such that in use, the barrel 110 extends towards and/or into a femoral neck 52. The barrel 110 includes a first superior cylindrical portion (or surface) 120 defining a first or superior passage 115*a* (shown in FIG. 2) and a second inferior cylindrical portion (or surface) 122 defining a second or inferior passage 115*b* (FIG. 2), the cylindrical surfaces extending parallel to one another and overlapping to some degree. The superior passage 115*a* and the inferior passage 115*b* also extend through corresponding portions of the plate 105, though such portions of the plate appear to blend into the barrel configuration in the present design, forming an upper lumen and a lower lumen through the fixation element 105. The superior cylindrical surface 120 and the inferior cylindrical surface 122 have approximately the same maximum diameter, but it is contemplated that the superior cylindrical surface may have a larger maximum diameter than the inferior cylindrical surface in some examples, and vice versa. Within each passage 115*a*, 115*b*, the internal diameter of the barrel 110 may define a corresponding shoulder. That is, as each passage 115*a*, 115*b* extends distally, the internal diameter of each of the cylindrical surfaces 120, 122 may transition abruptly from a first diameter to a second diameter smaller than the first diameter, thereby forming the shoulder within each respective passage 115*a*, 115*b*.

The fixation system 100 further includes a bolt 130*a* extending from a proximal end 132*a* to a distal end 134*a*, the bolt 130*a* sized and shaped for insertion into the superior passage 115*a*. The fixation system 100 also includes a lag screw 130*b* extending from a proximal end 132*b* to a distal end 134*b*, the lag screw 130*b* sized and shaped for insertion into the inferior passage 115*b*. The lag screw 130*b* has a threaded distal portion adjacent the distal end 134*b* which is inserted into the femur 50. In the illustrated example, the bolt 130*a* and lag screw 130*b* are generally similar in size and shape, however it is contemplated that they can vary in size and shape. For instance, the size of the bolt and lag screw may correspond to the size of the corresponding cylindrical portion and passage through which it extends. Thus, in examples in which the superior cylindrical portion is larger than the inferior cylindrical portion, the bolt may also be larger than the lag screw in length, diameter, etc.

Figure 3:
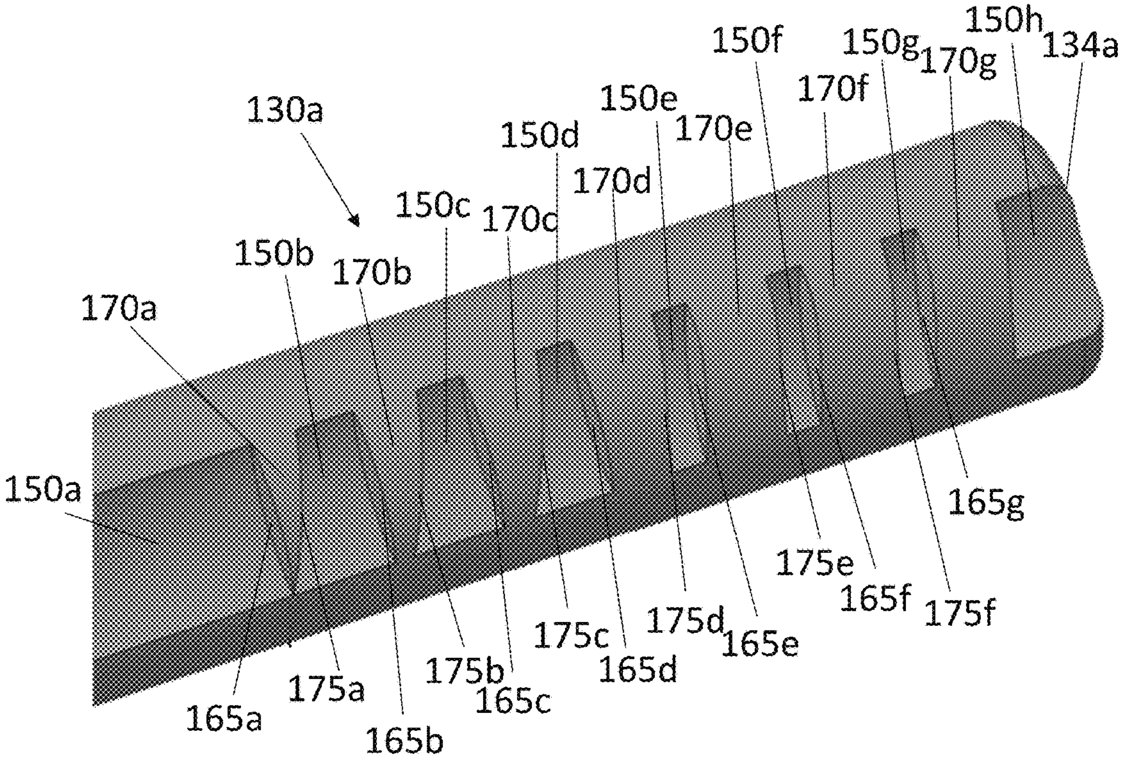
FIG. 3 is a close-up perspective view of a bolt of the fracture fixation system of FIG. 1
Figure 4:
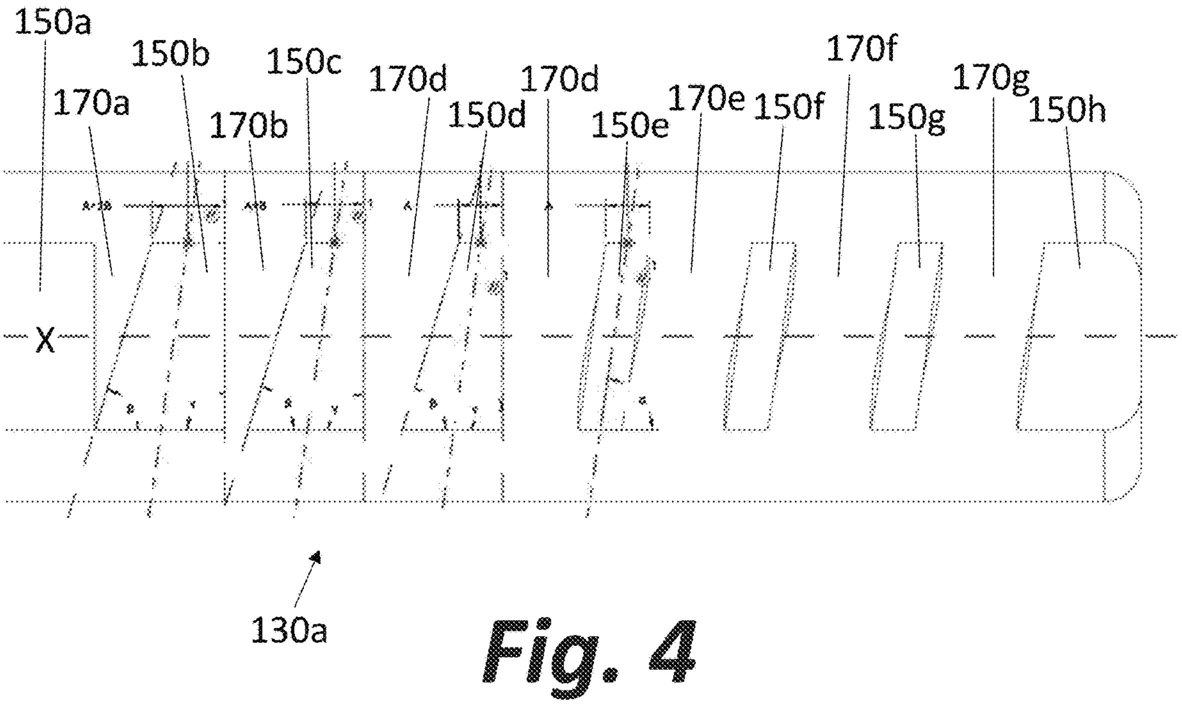
FIG. 4 is a bottom view of the bolt of FIG. 3.

As shown in FIGS. 3-4, a lateral side of the bolt 130*a* defines a plurality of recesses 150*a*-150*g* which together form a negative threading adapted to receive a thread 180 of the lag screw 130*b*. The bolt 130*a* includes a first proximal-most recess 150*a* which is elongate relative to the other recesses and essentially forms a channel leading up to recesses 150*b*-150*g*. Each of the recesses 150*a*-150*h* are separated by a respective section or ridge 170*a*-170*g*. That is, first recess 150*a* and second recess 150*b* are separated by first ridge 150*a*, second recess 150*b* and third recess 150*c* are separated by second ridge 170*b*, etc. The first recess 150*a* allows for receipt of the lag screw 130*b* without interference with the thread 180 during insertion, as will be described further below. The second, third and fourth recesses 150*b*-150*d* define a first group of recesses which vary in size and shape from each other as well as the other recesses. The first group of recesses may also be referred to as the transition portion. The fifth, sixth and seventh recesses 150*e*-150*g* define a second group of recesses which are consistent in size and shape relative to each other, but are a different size and shape than the other recesses 150*a*-150*d*, 150*h*. The second group of recesses 150*e*-150*g* are positioned distally along the bolt 130*a* (i.e., closer to the distal end 134*a*) relative to the first group of recesses 150*b-d*.

Each ridge 170*a*-170*g* protrudes radially outward from a central longitudinal axis of the bolt 130*a* relative to each of the plurality of recesses 150*a*-150*h* and defines a corresponding pair of opposing sidewalls which bound a recess adjacent the respective ridge. Each ridge therefore has a proximal-facing sidewall (i.e., facing toward the proximal end 132*a* of the bolt 130*a*) and a distal-facing sidewall (i.e., facing toward the distal end 134*a* of the bolt 130*a*) opposite the proximal-facing sidewall. More specifically, first ridge 170*a* has a first proximal-facing sidewall 165*a* and a second distal-facing sidewall 175*a*, second ridge 170*b* has a third proximal-facing sidewall 165*b* and a fourth distal-facing sidewall 175*b*, etc.

Each recess 150*a*-150*h* spans a length between the pair of surrounding ridges along a direction of the central longitudinal axis of the bolt 130*a*. Similarly, each ridge 170*a*-170*g* spans a length between the pair of surrounding recesses along a direction of the central longitudinal axis of the bolt 130*a*. As noted above, fifth, sixth and seventh recesses 150*e*-150*g* have the same length as each other, and accordingly, fifth, sixth and seventh ridges 170*e*-170*g* also have the same length as each other. Meanwhile, first, second, third and fourth ridges 170*a*-170*d* each have different lengths relative to one another when measured along the central longitudinal axis of the bolt 130*a*. Similarly, second, third and fourth recesses 150*b*-150*d* each have different lengths relative to one another when measured along a direction of the central longitudinal axis of the bolt 130*a*. In other words, first, second, third and fourth ridges 170*a*-170*d* and second, third and fourth recesses 150*b*-150*d* each have varying lengths that taper in a direction that is generally perpendicular to their length. A comparison of these lengths can be made when considered along a particular axis as indicated above. This is described further below.

Each recess 150*a*-150*h* defines a width in a direction transverse to the above-described length, and a magnitude of the length of each recess of the first group of the plurality of recesses 150*b*-150*d* varies along the width of the respective recess. Similarly, each ridge 170*a*-170*g* also defines a width in the direction transverse to the above-described length, and a magnitude of the length of ridges 170*a*-170*d* varies along the width of the respective ridge. More specifically, the length of each recess among the first group of the plurality of recesses 150*b*-150*d* tapers along the width of the respective recess, and the length of ridges 170*a*-170*d* tapers along the width of the respective ridge. The length of the recesses 150*b*-150*d* tapers in a first direction along the width direction and the length of the ridges 170*a*-170*d* tapers in a second direction along the width direction opposite the first direction.

The taper of the first group of the plurality of recesses 150*b*-150*d* is formed because the proximal-facing sidewall of each recess extends along a plane that is substantially perpendicular to the central longitudinal axis of the bolt 130*a*, whereas the distal-facing sidewall of each recess extends along a plane transverse to the central longitudinal axis of the bolt 130*a* and forms an acute angle with the central longitudinal axis as shown in FIG. 4. Thus, the plane of each proximal-facing sidewall is nonparallel to the plane of each distal-facing sidewall of the same recess, thereby forming a taper in the length of the recess. More specifically, third sidewall 165*b*, fifth sidewall 165*c* and seventh sidewall 165*d* each extend along respective planes which are substantially perpendicular to the central longitudinal axis and therefore substantially parallel to each other. Second sidewall 175*a*, fourth sidewall 175*b* and sixth sidewall 175*c* extend along planes which are substantially parallel to each other, but intersect with the central longitudinal axis to form an acute angle. Accordingly, the degree of taper of the length is consistent among each of the first group of the plurality of recesses 150*b*-150*d*, though the overall lengths are different. With reference to the second group of the plurality of recesses 150*e*-150*g*, each of the sidewalls extend along planes that are substantially parallel to one another. That is, sidewalls 175*d*-175*f* and sidewalls 165*e*-165*g* extend along substantially parallel planes which form an acute angle with the central longitudinal axis as shown in FIG. 4.

Figure 5:
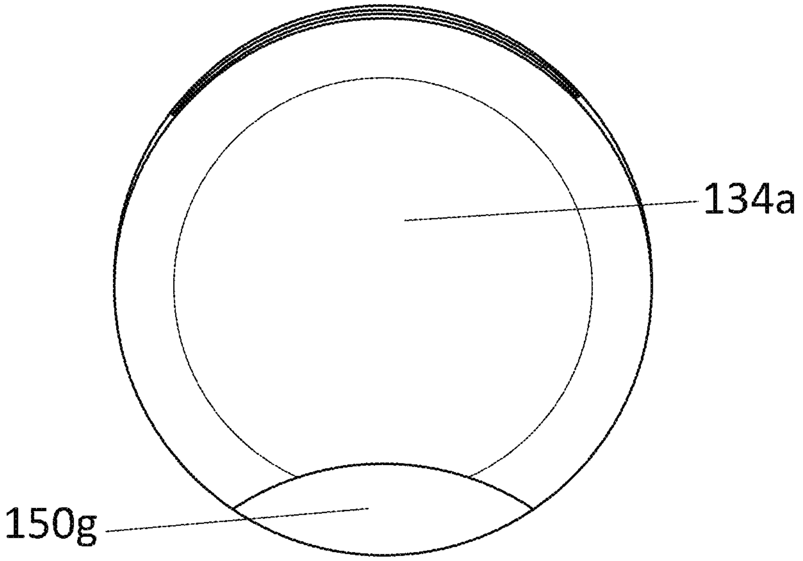
FIG. 5 is a front view of the bolt of FIG. 3.

FIG. 5 illustrates a distal view of bolt 130*a* showing recess 150*g*, which illustrates the radial depth into which each of the recesses extend and into which the thread 180 of the lag screw 130*b* can be received when the lag screw 130*b* is coupled to the bolt 130*a* as described in further detail below.

Figure 6:
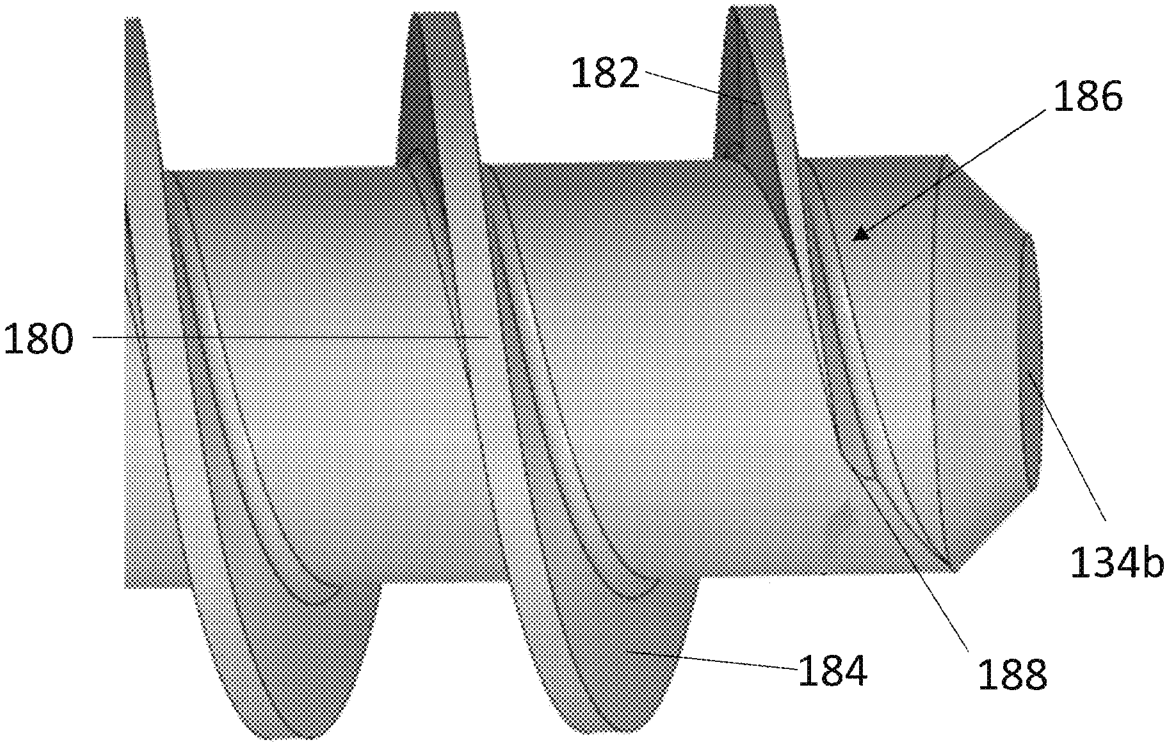
FIG. 6 is a close-up view of a distal portion of a lag screw of the fracture fixation system of FIG. 1.
Figure 7:
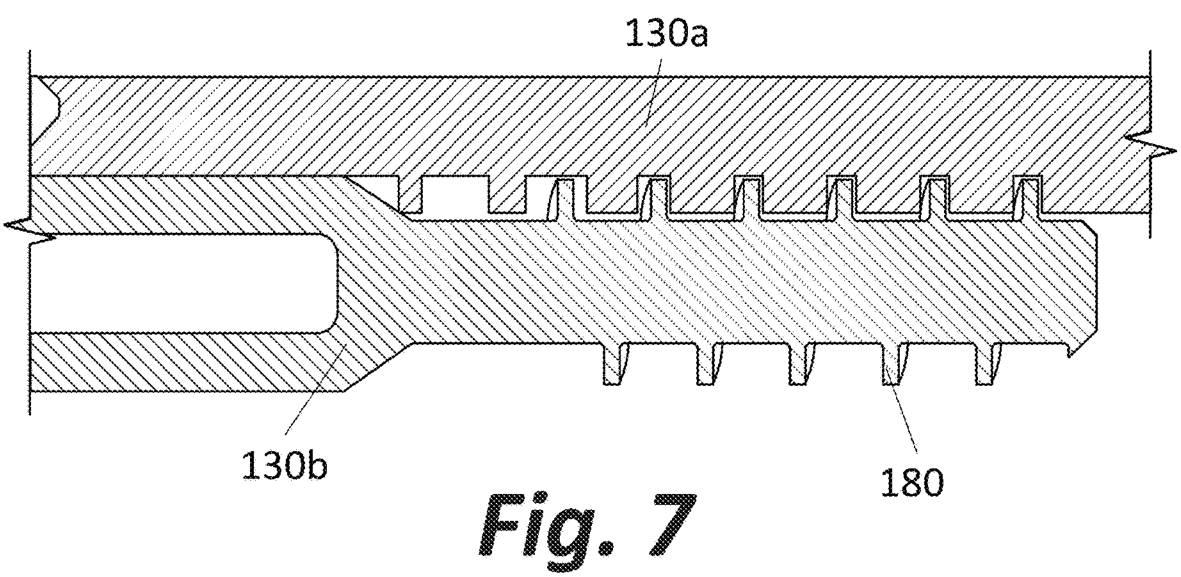
FIG. 7 is a close-up schematic view of the fracture fixation system of FIG. 1.
Figure 8:
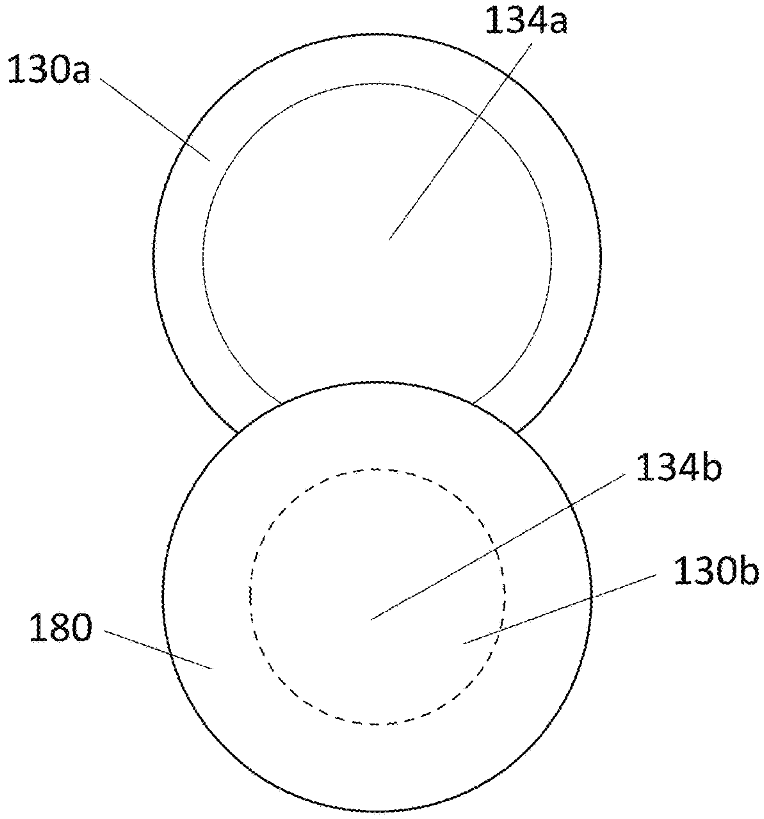
FIG. 8 is a front view of the fracture fixation system of FIG. 1.

FIG. 6 illustrates a portion of the lag screw 130*b* with the thread 180 extending helically along a length of the lag screw 130*b*, and FIG. 7 illustrates the lag screw 130*b* when coupled to the bolt 130*a*, e.g., with the thread 180 of the lag screw 130*b* engaging each of the plurality of recesses 150*b*-150*g* of the bolt 130*a*. The thread 180 of the lag screw 130*b* defines a thickness between a proximal-facing surface 182 and a distal-facing surface 184 of the thread 180, and the thickness of a distal portion 186 of the thread 180 tapers until the proximal-facing surface 182 and the distal-facing surface 184 of the thread 180 meet to form a distal edge 188 of the thread. FIG. 8 illustrates a distal view of the bolt 130*a* coupled to the lag screw 130*b* showing the thread 180 of the lag screw 130*b* mating with the negative thread of the bolt 130*a*. In the assembled configuration shown, each recess 150*b*-150*g* of the bolt 130*a* receives the helical thread 180 and each ridge 170*a*-170*g* of the bolt 130*a* protrudes into the corresponding spaced defined between the thread 180 along the lag screw 130*b*. The sizes and shapes of the plurality of recesses 150*a*-150*h* and the ridges 170*a*-170*g* as described above promote alignment of the thread 180 with the recesses of the bolt 130*a* while the lag screw 130*b* is inserted through a long bone to be coupled to the fixation system 100, as will be described below in greater detail with reference to the method of insertion.

It is contemplated that the fracture fixation system 100 may be packaged as a kit. The kit may include the plate 105 and barrel 110 formed as a single component, along with a bolt 130*a* and a lag screw 130*b*. A separate kit may include an intramedullary nail with a bolt 130*a* and a lag screw 130*b*. Still another kit may include the plate 105 and barrel 110 formed as a single component, an intramedullary nail, a bolt 130*a*, and a lag screw 130*b*, thereby permitting the user to select the fixation structure of choice for a particular surgical scenario.

Figure 9:
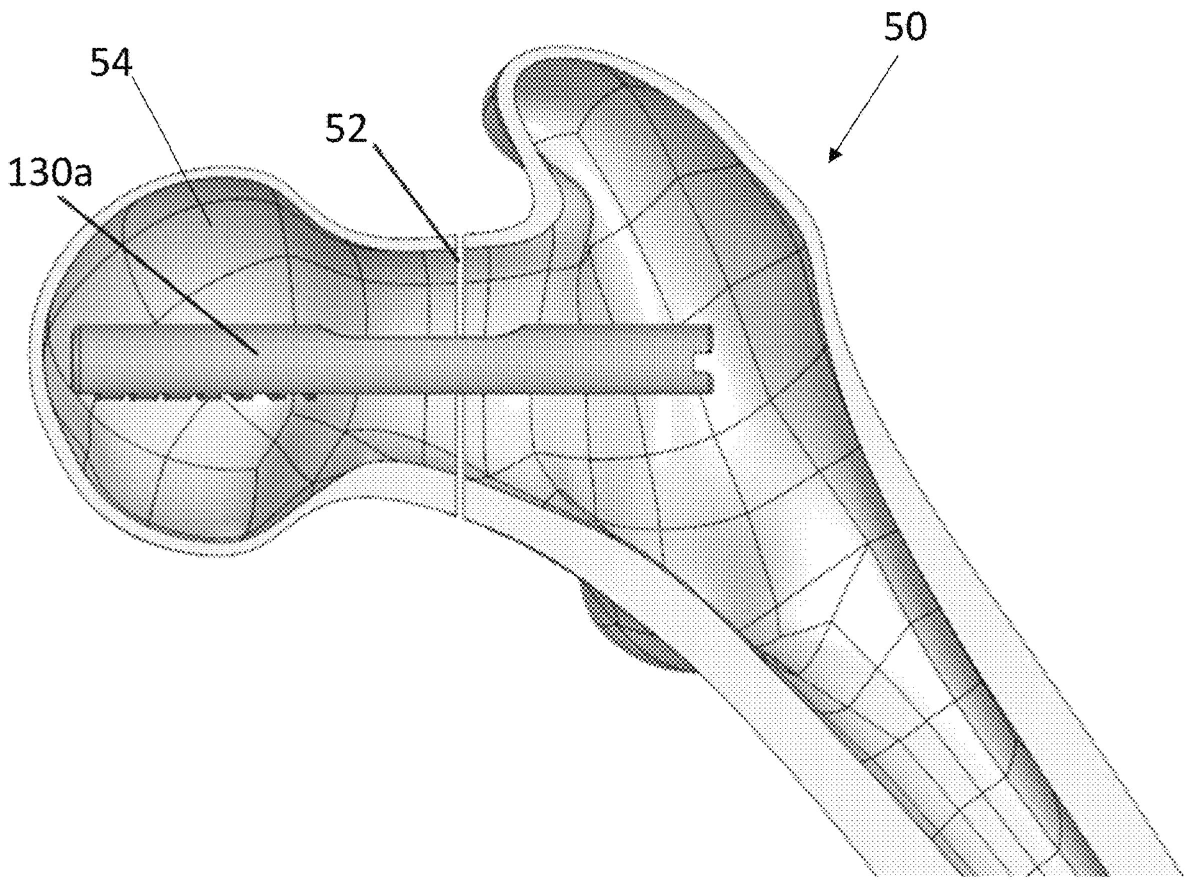
FIGS. 9-11 are method steps of using the fracture fixation system of FIG. 1 according to a first example.
Figure 10:
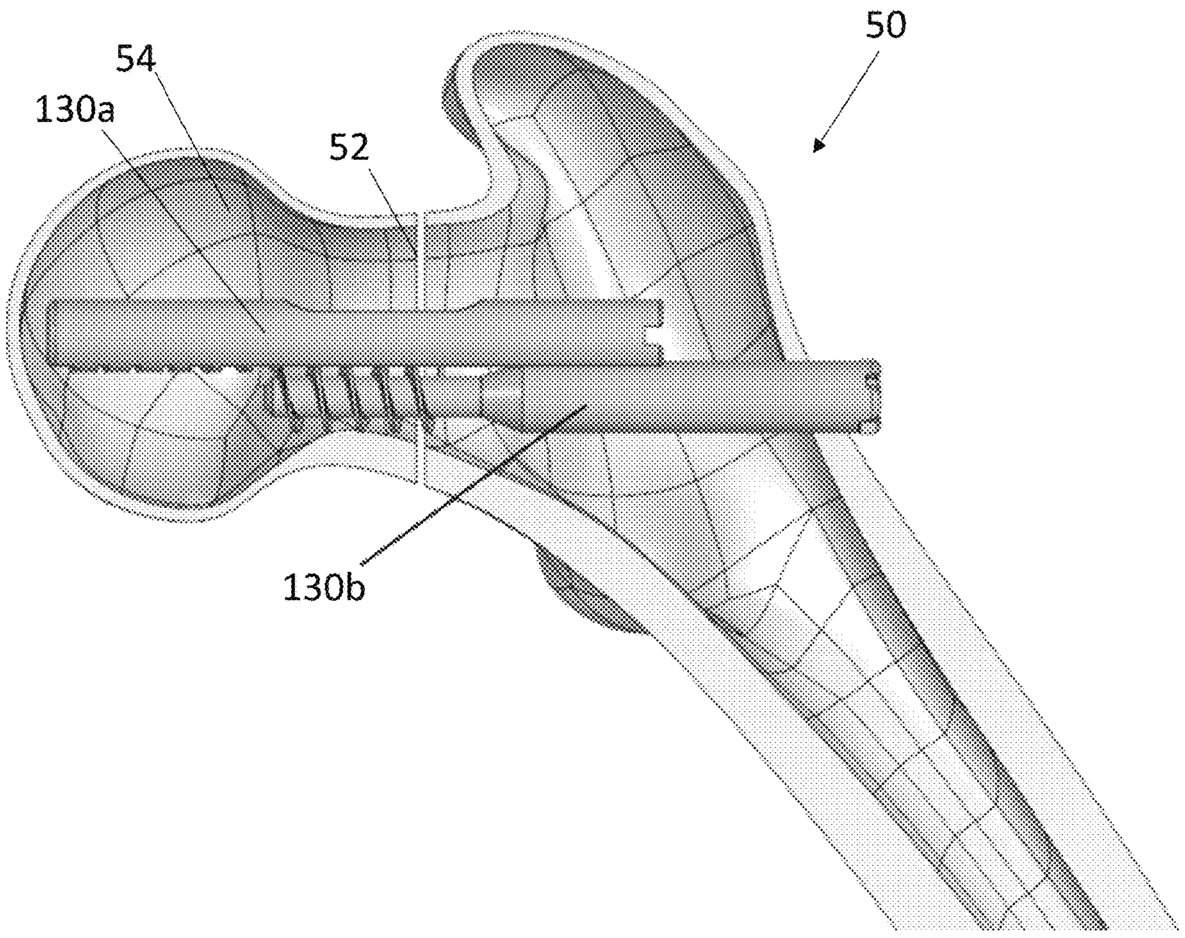
Figure 11:
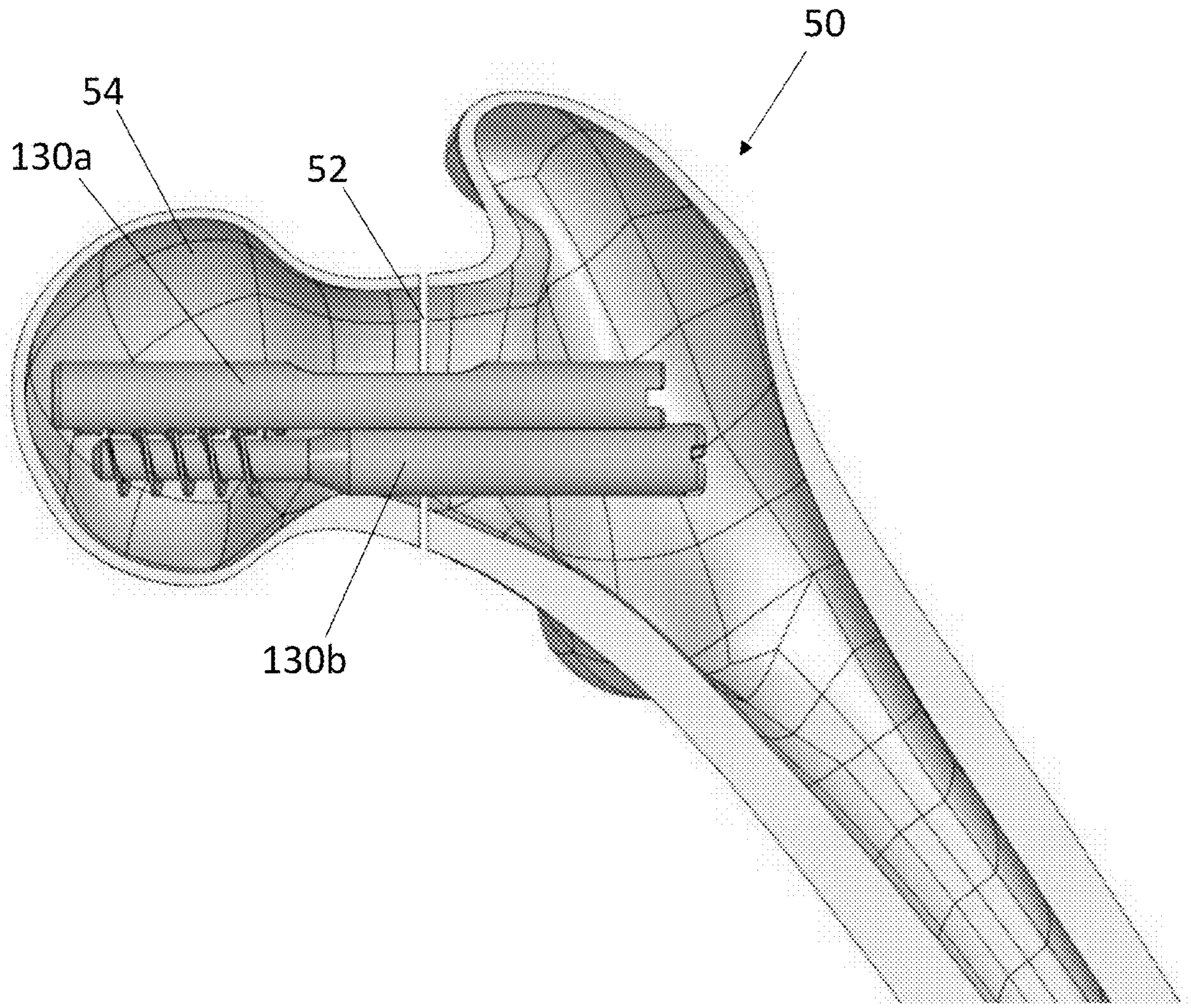

A method of using the fracture fixation system 100 is described with reference to FIGS. 9-11. A first pair of bores sized and shaped to receive the superior cylindrical portion 120 and the inferior cylindrical portion 122 of the barrel 110 may be prepared in the femur 50 as described in U.S. patent application Ser. No. 18/802,022 filed on Aug. 13, 2024, the disclosure of which is hereby incorporated by reference in its entirety. These bores may overlap as needed to mirror the shape of the outer perimeter of the barrel 110. The first pair of bores includes a first superior bore having a first diameter, the first superior bore being drilled to a first depth in the femoral neck. The first pair of bores further includes a first inferior bore having a second diameter, the first inferior bore also being drilled to approximately to the first depth. In the illustrated example, the first superior bore and the first inferior bore have the same diameter and are drilled to the same depth, however it is contemplated that the diameters and the depths of such bores may vary, particularly when the respective sizes of the first cylindrical portion 120 and the second cylindrical portion 122 of the fixation element 102 vary.

After the first pair of bores is drilled, a second pair of bores may be reamed. The second pair of bores are sized and shaped to receive at least a portion of the bolt 130*a* and lag screw 130*b*, respectively. The second pair of bores includes a second superior bore drilled within the diameter of the first superior bore to a depth greater than the depth of the first superior bore. The second pair of bores further includes a second inferior bored drilled within the diameter of the second inferior bore to a depth greater than the depth of the first inferior bore. That is, the second superior bore has a diameter smaller than the first superior bore and a depth greater than the first superior bore, and the second inferior bore has a diameter smaller than the first inferior bore and a depth greater than the first inferior bore. A K-wire may be used as a guide for the reamers and drills to follow.

After the bores are drilled, the fixation element 102 is applied or mounted to the femur 50 such that the superior cylindrical portion 120 and the inferior cylindrical portion 122 are inserted into the first superior bore and the first inferior bore, respectively, and the inner surface 107 of the plate 105 abuts an exterior surface of the femur 50. The fixation element 102 may be placed using a K-wire as a guide, for example, advancing the passages 115*a*, 115*b* along the K-wire.

Figure 14:
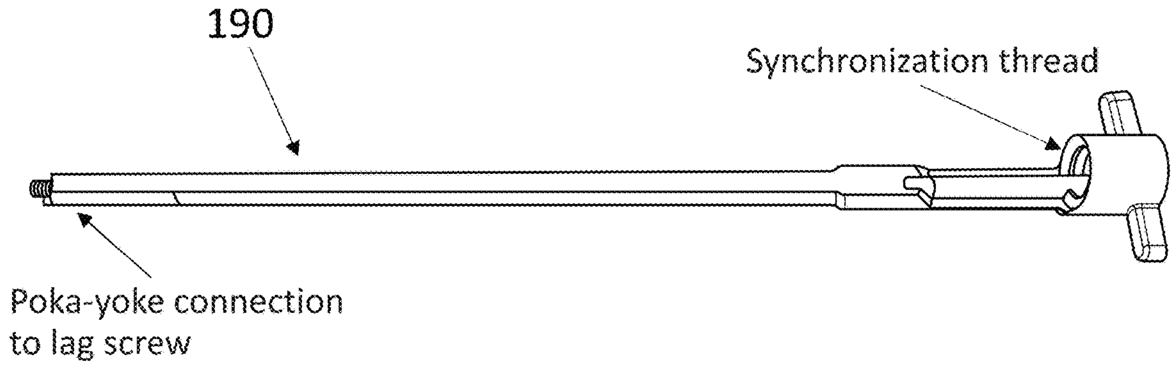
FIGS. 14-15 are insertion tools for the bolt and lag screw of the fracture fixation system of FIG. 1.

The bolt 130*a* is then inserted into the superior cylindrical portion 120 such that the distal end 134*a* of the bolt 130*a* extends into the second superior bore and into the neck 52 and head 54 of the femur 50 beyond the fracture in the femur. The bolt 130*a* may be inserted by placing the bolt 130*a* into or up against the superior passage 115*a* and engaging a tool, such as an insertion tool as shown in FIG. 14, with the proximal end of the bolt screw 130*a* to distally translate the bolt 130*a* through the passage 115*a* and into the second superior bore. During insertion, it is not necessary to rotate the bolt 130*a* about its axis.

The lag screw 130*b* is then inserted into the inferior cylindrical portion 122 such that the distal end 134*b* of the lag screw 130*b* ultimately extends into the second inferior bore and into the neck 52 and head 54 of the femur 50 beyond a fracture of the femur 50. The lag screw may be inserted through the inferior cylindrical portion 122 of the barrel 110, and upon entry into the inferior bore, the lag screw 130*b* may be rotated to continue distal advancement of the lag screw through the inferior bore. Advancement via rotation may continue as the lag screw 130*b* engages the first recess or transitional portion 150*a* of the bolt 130*a* such that the thread 180 of the lag screw 130*b* engages with the first recess 150*a*. Advancement via rotation may continue further as the thread 180 of the lag screw 130*b* will next enter the second recess 150*b*, third recess 150*c*, fourth recess 150*d*, etc.

Each of the recesses 150*b*-150*g* are sized and spaced apart in a manner such that a radial point on the thread 180 of the lag screw 130*b* will distally translate from one recess to a subsequent distal recess upon approximately 360 degrees of rotation of the lag screw 130*b*. For example, while the distal tip of the thread 180 is disposed in the second recess 150*b*, an approximate 360-degree rotation of the lag screw 130*b* will translate the lag screw 130*b* distally a distance such that the distal tip of the thread 180 is then disposed within the third recess 150*c* of the bolt 130*a*. The lag screw 130*b* may thus be rotated and distally advanced until the distal portion of the thread 180 is disposed within any one of the recesses, e.g., 150*f*, 150*g* or 150*h*.

It is appreciated that it may be unpredictable for an operator to know exactly where along an insertion axis of the lag screw 130*b* the distal end of the thread 180 will be located when the distal end of the thread 180 first contacts the negative thread of the bolt 130*a*. For example, as the lag screw 130*b* is rotated, the distal end of the thread 180 revolves around a 360-degree circle, and the distal portion of the thread 180 will engage the recesses 150*a*-150*h* as it reaches approximately the 180-degree position in its revolution (i.e. when it engages the negative thread). It is difficult for an operator to plan the precise axial positioning of the distal portion of the thread 180 when it reaches the approximate 180-degree position so that the thread can smoothly and seamlessly engage recesses of the bolt 130*a* when such recesses are all the same size. More specifically, it is difficult for an operator to plan for the distal portion of the thread 180 to engage the proximal most recess of the negative thread at the correct location, allowing frequent operations when the thread 180 runs into a ridge between the recesses.

In order to cure and avoid the potential obstacle of the distal portion of the thread 180 contacting the ridges (e.g., 170*a*) rather than the recesses (e.g., 150*b*), the ridges and recesses are sized and shaped accordingly as described herein. Three scenarios are described below to summarize the possible outcomes during insertion of the lag screw and its coupling to the bolt.

In each of the three scenarios, the thread 180 of lag screw 130*b* enters first recess 150*a* during insertion of the lag screw. The three scenarios diverge in their outcomes as the thread 180 approaches the first ridge 170*a*. In the first scenario, the lag screw is axially positioned such that as the distal end of the thread 180 axially aligns with the second recess 150*b*, the distal end of the thread is also reaching the 180-degree position of its revolution and thus passes smoothly through a central portion of the second recess 150*b* without contacting either of sidewalls 175*a* or 165*b*. The lag screw 130*b* may then be advanced further into the bone and the thread 180 may again pass through the third recess 150*c* and the fourth recess 150*d* without contacting sidewalls 175*b*, 165*c* or sidewalls 175*c*, 165*d*, respectively. In the first scenario, the lag screw will be aligned without any axial adjustments or forces imparted by the bolt 130*a* such that the lag screw may be further advanced so that the thread 180 enters and passes through any or all of the second group of recesses 150*e*-150*g*, which are sized and shaped to receive the thread 180 with a snug fit, e.g., without excess space in the recess when the thread is disposed therein.

Figure 12A:
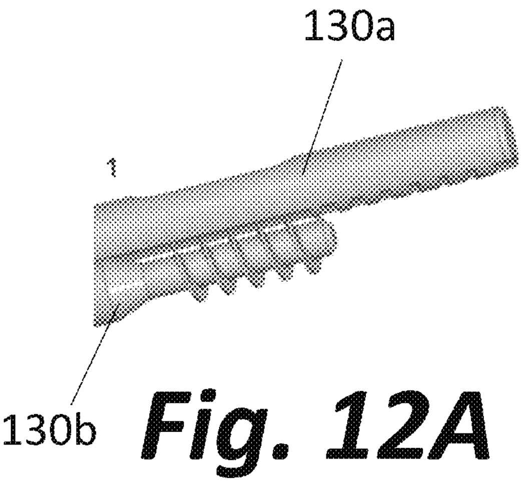
FIGS. 12A-12E illustrate stages of using the fracture fixation system of FIG. 1 according to a second example.
Figure 12B:
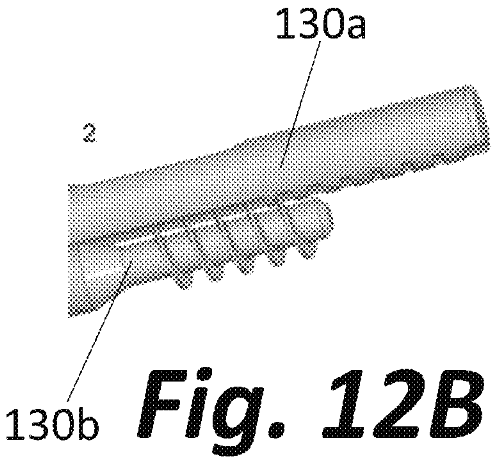
Figure 12C:
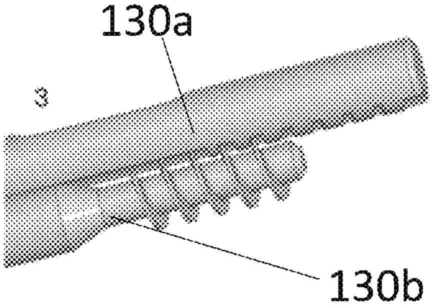
Figure 12D:
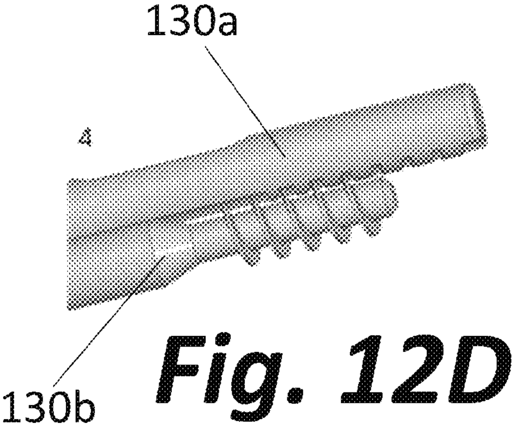
Figure 12E:
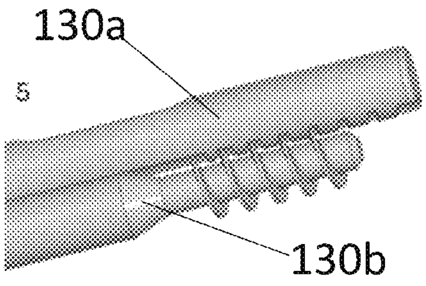

FIGS. 12A-12E illustrate a second scenario in which the bolt 130*a* imparts a distal force on the lag screw 130*b* during insertion of the lag screw 130*b* to align the thread 180 with the negative thread of the bolt 130*a* before the lag screw reaches the second group of recesses 150*e*-150*g*. This distal force facilitates an additional pure translation of the lag screw 130*b* in addition to the translation of the lag screw 130*b* that results solely from its rotation. As shown in FIG. 12B, a proximal-facing surface of the thread 180 contacts the second sidewall 175*a* of the first ridge 170*a* and propels the lag screw in the distal direction in addition to the normal advancement caused by the rotation of the lag screw in the first scenario. Put another way, the lag screw may be rotated and advanced distally along a generally consistent trajectory, and contact between the thread 180 and sidewall 175*a* may axially displace the lag screw from the trajectory further in the distal direction. A similar situation may then occur as the distal portion of the thread 180 approaches the third recess 150*c*, e.g., the proximal-facing surface of the thread 180 may contact the distal-facing sidewall 175*b* of second ridge 170*b* as shown in FIG. 12C. The contact between the thread 180 and sidewall 175*b* may further propel the lag screw 130*b* distally via translation even further from its original trajectory to push the lag screw 130*b* more closely to a state of alignment, the state of alignment being wherein the thread is positioned to pass smoothly through the second group of recesses 150*e*-150*g*. A similar situation may then again occur as the distal portion of the thread 180 approaches the fourth recess 150*d*, e.g., the proximal-facing surface of the thread 180 may contact the distal-facing sidewall 175*c* of the third ridge 170*c* as shown in FIG. 12D, thus further propelling the lag screw more closely to or finally into the state of alignment and enabling it to pass through the second group of recesses 150*e*-150*g* as shown in FIG. 12E. This all occurs because of the tapered lengths of the first group of the plurality of recesses 150*b*-150*d*, as well as the fact that successive lengths of the recesses get shorter in a distal direction. Recess 150*b* is the widest to gather the distal portion of the thread 180 and to propel it distally, passing it then onto recess 150*c* to perform the same added distal advancement, followed by the same in recess 150*d*. This gradual operation of recesses 150*b*-150*d* aligns and synchronizes the thread 180 of the lag screw 130*b* with the consistently pitched portion of the negative thread in the second group of recesses 150*e*-150*g*.

Figure 13A:
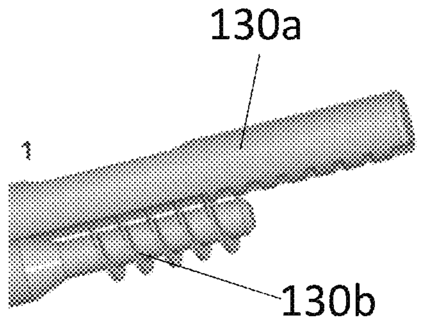
FIGS. 13A-13E illustrate stages of using the fracture fixation system of FIG. 1 according to a third example.
Figure 13B:
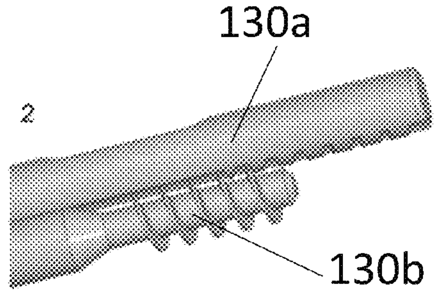
Figure 13C:
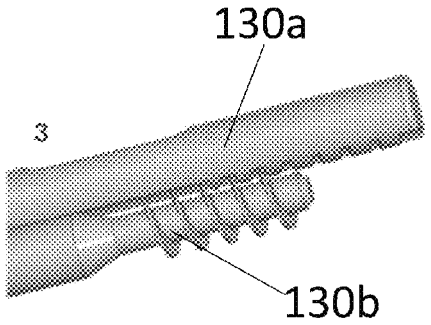
Figure 13D:
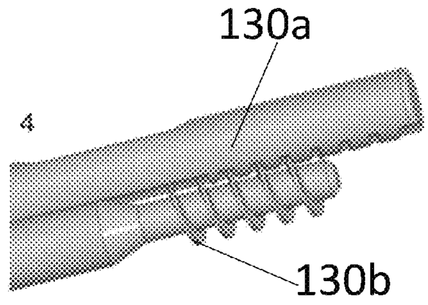
Figure 13E:
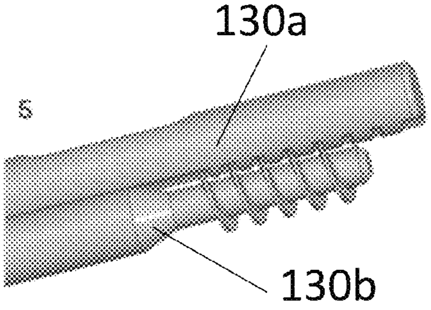

FIGS. 13A-13E illustrate a third scenario in which the bolt 130*a* imparts a proximal force on the lag screw 130*b* during insertion of the lag screw 130*b* to align the thread 180 with the negative thread of the bolt 130*a* before the lag screw reaches the second group of recesses 150*e*-150*g*. It is noted the movement of the lag screw is similar to that of the second scenario, except in the opposite direction (e.g., a proximal force to facilitate proximal movement, i.e. a subtracted pure translation of the lag screw 130*b*, relative to its original trajectory rather than distal movement). This subtracted pure translation reduces the translation of the lag screw 130*b* that results solely from its rotation. As shown in FIG. 13B, a distal-facing surface of the thread 180 contacts the third sidewall 165*b* of the second ridge 170*b* and imparts a proximal force on the lag screw 130*b* while it is being rotated and advanced through the bone. The proximal force imparted by the bolt 130*b* may counteract the distal advancement caused by rotation of the lag screw, and the axial position of the lag screw may only change slightly, if at all, during rotation of the lag screw while the thread contacts the sidewall. Put another way, the lag screw 130*b* may be rotated and advanced distally along a generally consistent trajectory, and contact between the thread 180 and the sidewall 165*b* may axially displace the lag screw from the trajectory in the proximal direction. A similar interface may then occur as the distal portion of the thread 180 approaches the third recess 150*c*, e.g., the distal-facing surface of the thread 180 may contact the proximal-facing sidewall 165*c* of the third ridge 170*c* as shown in FIG. 13C. The contact between the thread 180 and sidewall 165*c* may further hinder distal advancement of the lag screw and even further offset the lag screw from its original trajectory to pull the lag screw more closely to a state of alignment with the second group of recesses 150*e*-150*g*. A similar situation may then again occur as the distal portion of the thread 180 approaches the fourth recess 150*d*, e.g., the distal-facing surface of the thread 180 may contact the proximal-facing sidewall 165*d* of the fourth ridge 170*d* as shown in FIG. 13D, thus further hindering the lag screw more closely to or finally into the state of alignment and enabling it to pass through the second group of recesses 150*e*-150*g* as shown in FIG. 13E.

Figure 15:
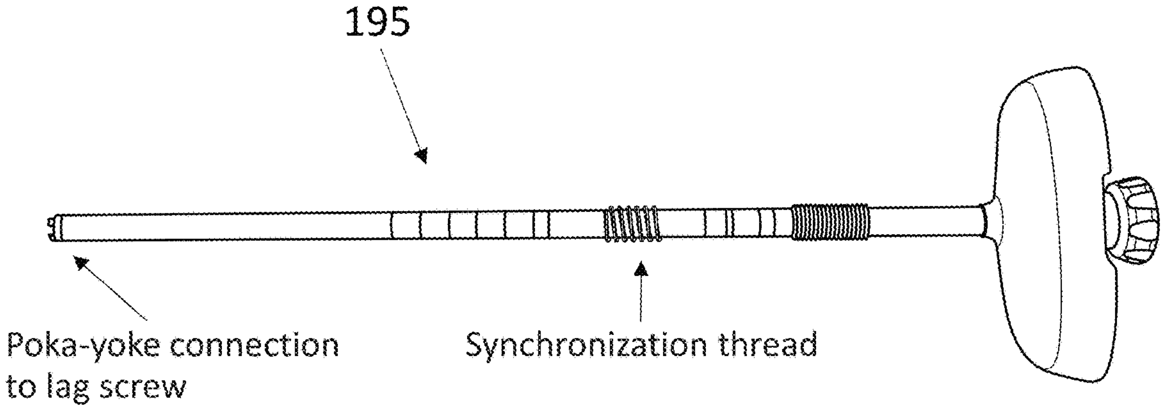
Figure 16:
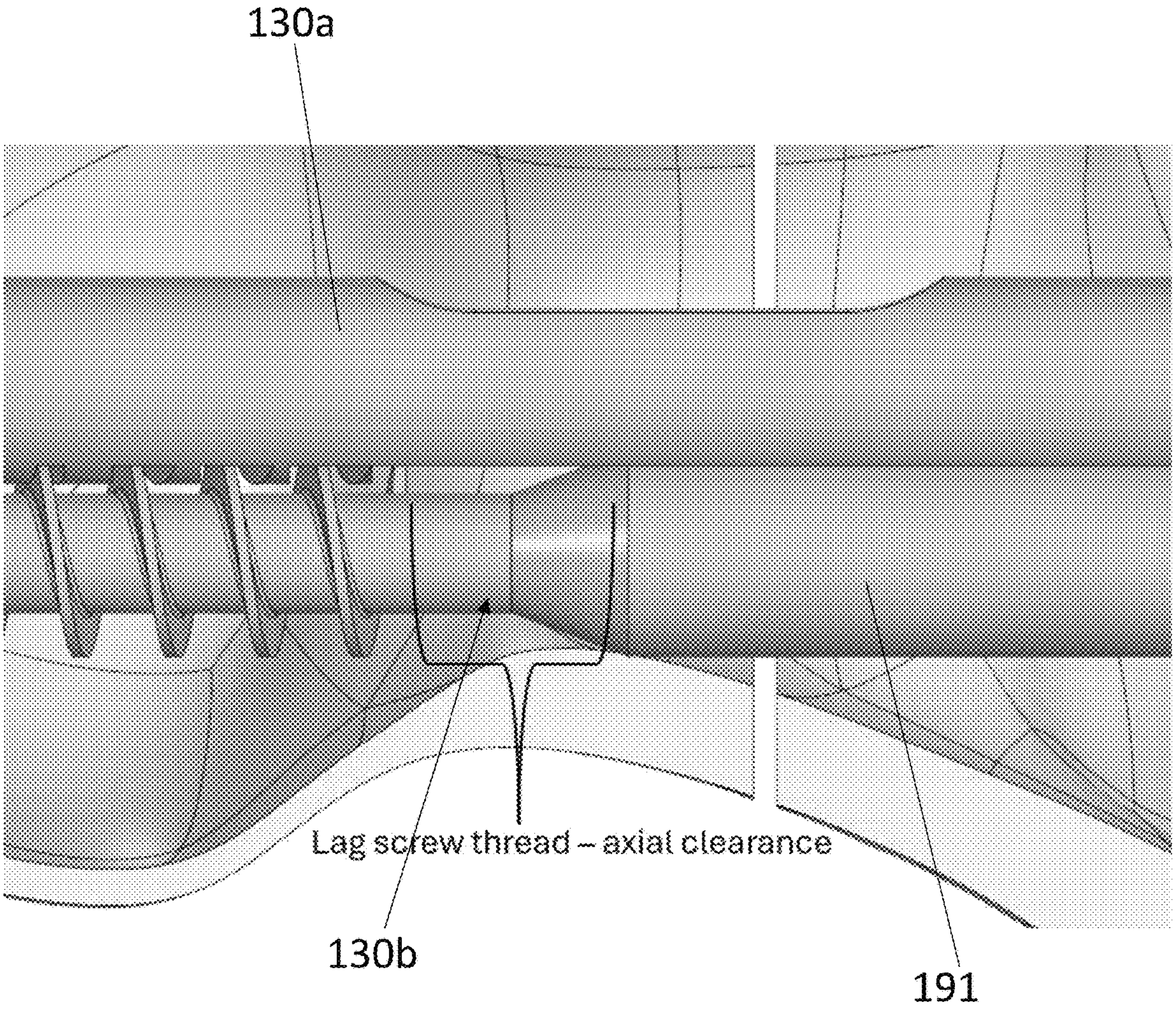
FIG. 16 is a close-up schematic view of the fracture fixation system of FIG. 1.

After the lag screw 130*b* is inserted to a desired axial position, e.g., the thread 180 of the lag screw 130*b* is disposed within several of recesses 150*b*-150*h*, the lag screw 130*b* and/or bolt 130*a* may be drawn or biased proximally to provide a lateral compressive force on the femoral head, thereby applying a compressive force to the fracture. Such a compressive force enhances the ability of the fracture to heal and promotes and facilitates bone growth. A desired axial position may be, for example, as shown in FIG. 16, wherein an entirety of the thread 180 is positioned distal to the femoral neck fracture. It is noted that a length of clearance is included between the proximal-most point of the thread 180 and the thickened portion 191 of the lag screw 130*b* having an increased cross-sectional diameter, which is beneficial to ensure that the thread is located distal to the fracture. This is to enable effective fracture compression by the lag screw 130*b* when the lag screw is pulled proximally. The clearance length may also help to avoid collision between the thickened portion 191 of the lag screw and the negative thread of the bolt. A bolt insertion instrument 190 as shown in FIG. 14 may be used for insertion of the bolt 130*a*. A lag screw insertion instrument 195 as shown in FIG. 15 may be used for insertion of the lag screw 130*b*. Insertion instruments 190, 195 couple detachably couple to each of bolt 130*a* and lag screw 130*b* for insertion into their respective passages and to prevent rotation of the bolt during insertion and rotation of the lag screw.

As noted above, the fracture fixation device 100 may alternatively be implemented with an intramedullary nail rather than the plate and barrel as described above. For example, an intramedullary canal of a long bone, such as a femur, may be reamed and an intramedullary nail inserted therein. The intramedullary nail may include a superior bore and an inferior bore and passages may be reamed and drill into the long bone forming a superior passage and an inferior passage through the superior bore and inferior bore of the nail, respectively, similar to those defined in the barrel described above. The bolt 130*a* may then be inserted into the superior passage and the lag screw 130*b* may subsequently be inserted into the inferior passage and coupled to the bolt in the manner described above.

As a result of the structures and methods described herein, a more securely and precisely aligned bolt and lag screw can be achieved despite the inherent variability in the early stages of the insertion process. The configuration of the negative thread in the lag screw facilitates the synchronization of the thread of the lag screw with at least the distal portion of the negative thread of the bolt. This is carried out despite the lack of visibility of the zone of interaction between the thread of the lag screw and the negative thread of the bolt, Resulting in a more consistent and secure implanted structure.

Figure 17:
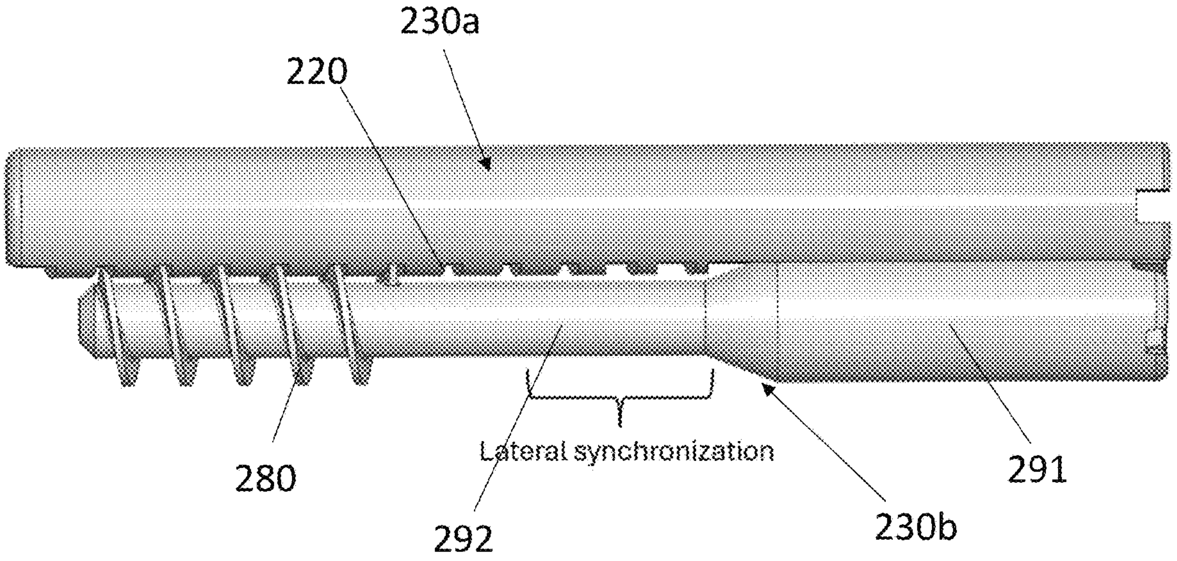
FIG. 17 is a schematic view of a bolt and lag screw assembly of a fracture fixation system according to another embodiment of the disclosure.

It should be appreciated that slight deviations and alterations from the system and method described above are also contemplated herein. For example, the orientation of the bolt and the lag screw may be reversed such that the bolt is inserted through the inferior passage or bore and the lag screw is inserted through the superior passage or bore. In further examples, the number of recesses defined on the lateral side of the bolt and forming the negative thread may deviate from the illustrated embodiment. Specifically, there may be a greater or lesser number of recesses belonging to the first group of recesses which have tapering lengths causing alignment and synchronization of the lag screw thread with the negative thread, and there may also be a greater or lesser number of recesses belong to the second group of recesses which have equal lengths. For instance, the embodiment illustrated in FIG. 17 includes 13 recesses 270 defining the negative thread of the bolt 230*a*, and the lag screw 230*b* has a correspondingly elongated neck portion 292 accommodating for the increased number of recesses to allow the thread 280 to reach the distal portion of the negative thread while preventing the thickened portion 291 from interfering with the negative thread of the bolt 230*a*.

Figure 18:
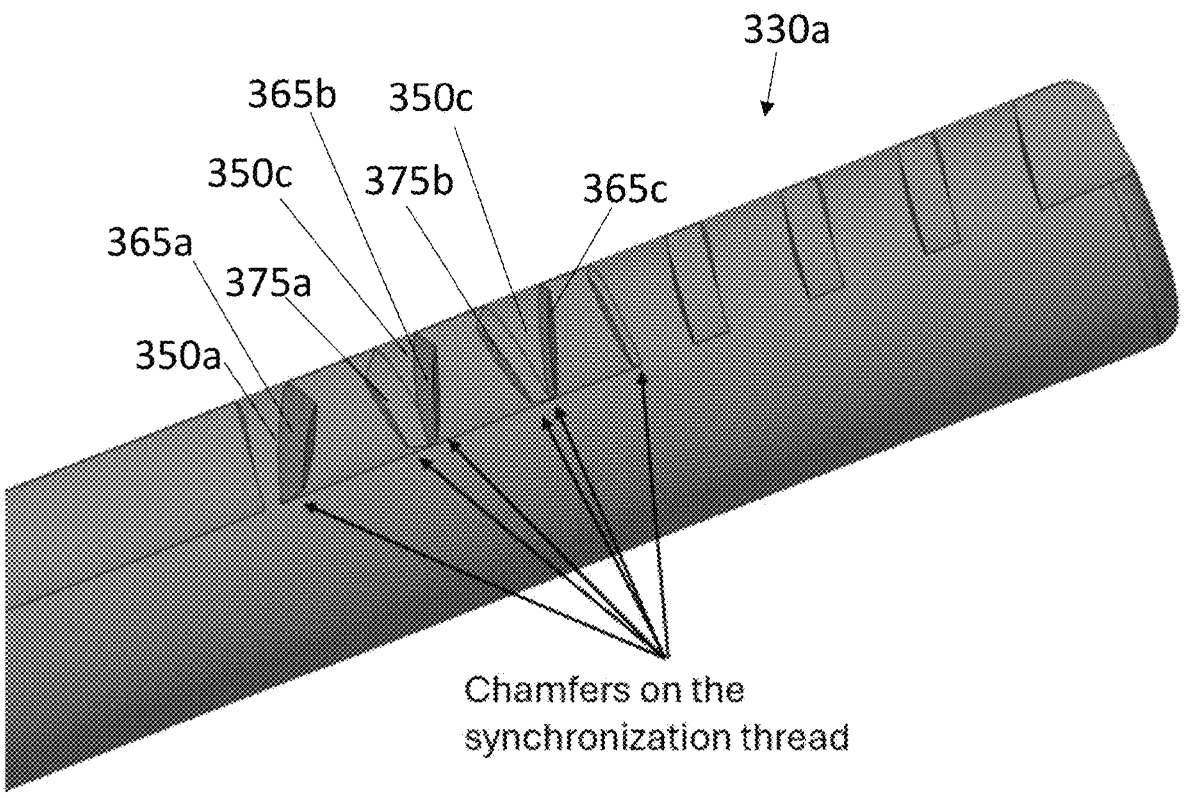
FIG. 18 is a bolt of a fracture fixation system according to another embodiment of the disclosure.
Figure 19:
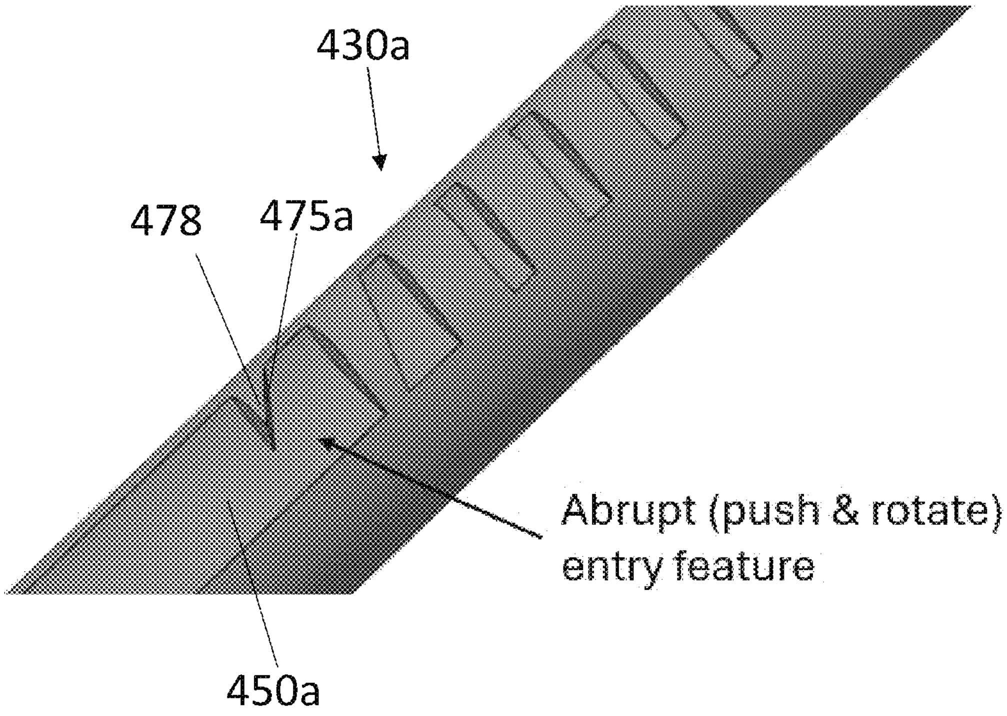
FIG. 19 is a bolt of a fracture fixation system according to another embodiment of the disclosure.

Furthermore, the angle of the planes along which the sidewalls extend relative to the central longitudinal axis of the bolt may vary from the illustrated embodiment. Similarly, the degree at which the lengths of the ridges and recesses belonging to the first group of recesses taper may also vary from the illustrated embodiment. For example, the second recess 150*b* may have a larger taper thereby increasing the length on the side of the recess in which the thread of the lag screw enters to increase the amount of trajectory adjustment imparted by the respective sidewalls. In the example illustrated in FIG. 18, the sidewalls 365*a*-365*c*, 375*a*-375*b* of the first group of recesses 350*a*, 350*b*, 350*c* of the bolt 330*a* include tangential chamfers, which may help with the axial retention between the lag screw and bolt during alignment and synchronization of the lag screw with respect to the bolt. In the example illustrated in FIG. 19, the bolt 430*a* includes a protrusion 478 extending into the first recess 450*a* which includes a distal facing sidewall 475*a* extending at a steeper angle than that of the bolt 130*a* and causes contact between the lag screw thread and the sidewall 475*a* to propel the lag screw a relatively greater distance and thereby synchronize the lag screw thread with the bolt more abruptly.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A fracture fixation system, comprising:

an implant defining a transverse bore extending along a bore axis, the bore being defined by first and second passages that each extend along an axis that is parallel to the bore axis;

a lag screw configured to be inserted through the second passage, wherein a distal portion of the lag screw includes a thread; and a bolt configured to be inserted through the first passage, wherein a side of the bolt defines a negative thread adapted to receive the thread of the lag screw, wherein the negative thread of the bolt includes a plurality of recesses each disposed between a pair of ridges of the bolt, each of the ridges protruding radially outward from a central longitudinal axis of the bolt relative to the plurality of recesses, and wherein each recess spans a length along a direction of the central longitudinal axis between the pair of surrounding ridges, and wherein the plurality of recesses includes a first group of recesses having varying lengths relative to each other and a second group of recesses having equal lengths relative to each other, and wherein the second group is positioned distal to the first group along the direction of the central longitudinal axis of the bolt.

2. The fracture fixation system of claim 1, wherein the implant includes a plate and a barrel, the plate having an outer surface and an inner surface for placement against an exterior surface of a bone, and the barrel extending along the bore axis and having a peripheral wall, the first and second passages extending through the barrel.

3. The fracture fixation system of claim 1, wherein the implant is an intramedullary nail.

4. The fracture fixation system of claim 1, wherein each recess defines a width in a direction transverse to the length, and wherein a magnitude of the length of each recess of the first group of the plurality of recesses varies along the width of the respective recess.

5. The fracture fixation system of claim 1, wherein the plurality of recesses are sized and spaced such that engagement of the thread of the lag screw with the negative thread causes axial displacement of the lag screw relative to the bolt to align the thread of the lag screw with the plurality of recesses when the lag screw is being coupled to the bolt.

6. A fracture fixation system, comprising:

an implant defining a transverse bore extending along a bore axis, the bore being defined by first and second passages that each extend along an axis that is parallel to the bore axis;

a lag screw configured to be inserted through the second passage, wherein a distal portion of the lag screw includes a thread; and a bolt configured to be inserted through the first passage, wherein a side of the bolt defines a negative thread adapted to receive the thread of the lag screw, wherein the negative thread of the bolt includes a plurality of recesses each disposed between a pair of ridges of the bolt, each of the ridges protruding radially outward from a central longitudinal axis of the bolt relative to the plurality of recesses, and wherein each recess spans a length along a direction of the central longitudinal axis between the pair of surrounding ridges, and wherein each recess defines a width in a direction transverse to the length, wherein the plurality of recesses includes a first group of recesses having lengths tapering along their respective widths, and wherein the plurality of recesses includes a second group of recesses having lengths which are constant along their respective widths.

7. The fracture fixation system of claim 6, wherein the second group of recesses is positioned distal to the first group of recesses along a length of the bolt.

8. The fracture fixation system of claim 6, wherein the plurality of recesses are sized and spaced such that engagement of the thread of the lag screw with the negative thread causes axial displacement of the lag screw relative to the bolt to align the thread of the lag screw with the plurality of recesses when the lab screw is being coupled to the bolt.

9. A method of using a fracture fixation system, comprising:

drilling into a bone a first superior bore having a first diameter to a first depth;

drilling into the bone a first inferior bore having a second diameter to a second depth;

installing an implant to the bone;

inserting a bolt into a transverse bore defined through the implant such that a distal end of the bolt extends into one of the first superior bore and the first inferior bore; and inserting a lag screw into the transverse bore defined through the implant such that a distal end of the lag screw extends into the other one of the first superior bore and the first inferior bore, wherein inserting the lag screw includes rotating the lag screw to advance the lag screw distally relative to the bolt such that a thread of the lag screw engages with negative thread of the bolt, and wherein the lag screw is advanced along a trajectory, and wherein the negative thread of the bolt is sized and shaped to axially displace the lag screw from the trajectory to align the thread of the lag screw with the negative thread of the bolt.

10. The method of claim 9, wherein installing the implant to the bone includes placing an inner surface of a plate against an exterior surface of the bone, and inserting a peripheral wall of a barrel into the first superior bore and the first inferior bore.

11. The method of claim 9, wherein installing the implant to the bone includes inserting an intramedullary nail in an intramedullary canal of the bone.

12. The method of claim 9, wherein the negative thread of the bolt includes a plurality of recesses spaced apart along a length of the bolt, and wherein advancing the lag screw includes engaging the thread of the lag screw with a proximal recess of the plurality of recesses.

13. The method of claim 12, wherein advancing the lag screw includes contacting the thread of the lag screw with a surface bounding the first recess to impart an axial force on the lag screw as the lag screw is rotated.

14. The method of claim 13, wherein the surface bounding the first recess is at a proximal end of the first recess and imparts a distal axial force on the lag screw.

15. The method of claim 13, wherein the surface bounding the first recess is at a distal end of the first recess and imparts a proximal axial force on the lag screw.

16. The method of claim 9, further comprising pulling the lag screw proximally to compress a femoral neck fracture.

* * * * *